(12) United States Patent
Huang

(10) Patent No.: US 11,911,133 B2
(45) Date of Patent: Feb. 27, 2024

(54) OPERATION METHOD AND DEVICE FOR PHYSIOLOGICAL HEALTH DETECTION

(71) Applicant: SHANGHAI HARVEST INTELLIGENCE TECHNOLOGY CO., LTD., Shanghai (CN)

(72) Inventor: Jiandong Huang, Shanghai (CN)

(73) Assignee: SHANGHAI HARVEST INTELLIGENCE TECHNOLOGY CO., LTD., Shanghai (CN)

( * ) Notice: Subject to any disclaimer, the term of this patent is extended or adjusted under 35 U.S.C. 154(b) by 1032 days.

(21) Appl. No.: 16/643,584

(22) PCT Filed: Apr. 2, 2018

(86) PCT No.: PCT/CN2018/081593
§ 371 (c)(1),
(2) Date: Mar. 1, 2020

(87) PCT Pub. No.: WO2019/041810
PCT Pub. Date: Mar. 7, 2019

(65) Prior Publication Data
US 2020/0229709 A1    Jul. 23, 2020

(30) Foreign Application Priority Data

Aug. 30, 2017 (CN) .......................... 201710760718.4

(51) Int. Cl.
*A61B 5/0205* (2006.01)
*A61B 5/026* (2006.01)
(Continued)

(52) U.S. Cl.
CPC ............ *A61B 5/0205* (2013.01); *A61B 5/029* (2013.01); *A61B 5/0261* (2013.01);
(Continued)

(58) Field of Classification Search
CPC ..... A61B 5/0205; A61B 5/318; A61B 5/0261; A61B 5/029; A61B 5/14552;
(Continued)

(56) References Cited

U.S. PATENT DOCUMENTS 8,886,334 B2 * 11/2014 Ghaffari ................. A61B 5/145
607/115
9,554,484 B2 *  1/2017 Rogers ................... H05K 1/189
(Continued)

FOREIGN PATENT DOCUMENTS

WO    WO-2010102310 A2 *  9/2010 ........... A61B 5/0091

*Primary Examiner* — Kwin Xie

(57) ABSTRACT

Provided are an operation method and device for physiological health detection, wherein by arranging a body part identification area on a display unit, and arranging a sensing unit below the body part identification area, when a body part of a user is close to the body part identification area, the sensing unit may capture optical signal information reflected by the body part, and a processing unit may obtain, according to the optical signal information reflected by the body part, physiological health information corresponding to the body part, and the physiological health information may be displayed on the display unit. Compared with the existing method of a mobile device additionally arranging a sensor outside a display screen region, the present invention facilitates user operations and improves the user experience, and the whole thickness of the mobile device may also be effectively reduced, thereby enabling the mobile device to be lighter and thinner and satisfy the requirements of the market.

16 Claims, 12 Drawing Sheets

(51) Int. Cl.
  *A61B 5/029* (2006.01)
  *A61B 5/1455* (2006.01)
  *A61B 5/00* (2006.01)
  *H01L 27/12* (2006.01)
  *A61B 5/021* (2006.01)
  *A61B 5/024* (2006.01)

(52) U.S. Cl.
  CPC ........ *A61B 5/14552* (2013.01); *A61B 5/4872* (2013.01); *A61B 5/742* (2013.01); *A61B 5/7405* (2013.01); *H01L 27/12* (2013.01); *A61B 5/02141* (2013.01); *A61B 5/02433* (2013.01); *A61B 2562/0233* (2013.01)

(58) Field of Classification Search
  CPC ..... A61B 5/4872; A61B 5/7405; A61B 5/742; A61B 5/02141; A61B 5/02433; A61B 2562/0233; H01L 27/12
  USPC ........................................................ 345/207
  See application file for complete search history.

(56) References Cited

U.S. PATENT DOCUMENTS

| | | | | |
|---|---|---|---|---|
| 2013/0316487 A1* | 11/2013 | de Graff | .................. | A61B 1/04 438/66 |
| 2016/0058375 A1* | 3/2016 | Rothkopf | ............. | G04G 21/025 600/323 |
| 2017/0136264 A1* | 5/2017 | Hyde | ..................... | G16H 50/30 |
| 2017/0164876 A1* | 6/2017 | Hyde | ..................... | A61B 5/1118 |
| 2018/0001184 A1* | 1/2018 | Tran | ....................... | G16H 50/20 |

* cited by examiner

Top view of light detection film

Side view of light detection film

Film substrate

G : Gate

Top view of light detection film

Side view of light detection film

Film substrate

G : Gate

Insulating layer

OPERATION METHOD AND DEVICE FOR PHYSIOLOGICAL HEALTH DETECTION

BACKGROUND OF THE INVENTION

1. Field of the Invention

The present disposure relates to application field of electronic equipment, and more particularly relates to an operation method and operation device of physiological health detection

2. Description of the Prior Art

With the development of science and technology and the advancement of technology, the touch display panels have been widely used in devices requiring human-computer interaction interfaces, such as operation screens of industrial computers, tablet computers, touch screens of smart phones, etc.

A liquid crystal display (LCD) screen or an active array organic light-emitting diode (AMOLED) display screen, etc., both of them scan and drive a single pixel through a film transistor (TFT) structure to realize the display function of the on-screen pixel array. The main structure for forming the TFT switching function is a semiconductor field effect transistor (FET), and the well-known semiconductor layer is mainly made of amorphous silicon, polycrystalline silicon, indium gallium zinc oxide (IGZO), or an organic compound mixed with carbon nano materials.

Since the structure of a photo diode may also be ready by such semiconductor materials and the production equipment is also compatible with the production equipment of the TFT array, so in recent years the TFT photo diode is produced by the TFT array manufacturing method and is widely used in X-ray sensing flat panel devices, such as those described in the patents CN103829959B and CN102903721B of the People's Republic of China.

In fact, in the application of light detection, the TFT structure has the characteristics of light-sensitive function: Generally, when the TFT is controlled to be turned off by the gate voltage, no current flows from the source to the drain. However, when the TFT is exposed to the light, the electron-hole pair in the semiconductor is excited by the energy of the light, and the field effect of the TFT structure will cause the electron-hole pair to be separated, thereby causing the TFT to leak current. This leakage current characteristics make TFT arrays be gradually applied to the technology of light detection or infrared light detection, such as described in the patents of the People's Republic of China CN100568072C and CN105044952A. If such a well-known TFT light sensing array film is arranged in the display structure, it can be used as an implementation solution for integrating the light detection function in the display.

In light detection applications, there is still much room for improvement in the structure of the traditional TFT device. Under normal circumstances, the lighting may include changes of more than 3 orders of magnitude (60 dB) from the darkest area to the brightest area. For infrared light detection applications using TFT leakage current operating in the shutdown region, it is necessary to increase the photosensitivity of the TFT and the signal-to-noise ratio (SNR) of the device, and it is also necessary to avoid increasing the complexity and power consumption of the overall system.

In summary, for wearable electronic devices, there is still much room for improvement in human-computer interaction interface technology. Take physical health data detection as an example, currently it mainly depends on the interaction between the terminal and the IoT device to complete. It requires users to wear additional IoT devices (such as smart bracelets, smart watches, etc.) in order to detect the user's physical health data. It requires users to wear additional IoT devices (such as smart bracelets, smart watches, etc.) in order to detect the user's physical health data. This also increases device costs. If the physiological health data detection function directly implemented on the terminal device is required, it is necessary to place an additional sensor (such as a light sensor) on the terminal and outside the screen area. The way increases the difficulty of processing and assembling of the terminal on the one hand, and also increases the thickness of the terminal as a whole, limiting the development of thinning and rollable applications of the terminal screen.

SUMMARY OF THE INVENTION

For this reason, it is necessary to provide a technical solution for physiological health detection to solve the problem of the difficulty of processing and assembling of the terminal, limiting the development of thinning and rollable applications of the terminal screen due to placing an additional sensor on the terminal and outside the screen area if the physiological health data detection function directly implemented on the terminal device is required.

To achieve the above objective, the inventor provides an operation method for physiological health detection. The method is applied to an operation device for physiological health detection. The operation device includes a display unit, a sensing unit and a processing unit. A body part identification area is disposed on the display unit. The sensing unit is disposed below the body part identification area. The operation method includes:

generating an optical signal and receiving the optical signal reflected by a body part of a user by the sensing unit to capture a body part information of the user and recording an optical signal information reflected by the body part when the sensing unit receiving a light source trigger signal;

obtaining a physiological health information corresponding to the body part based on the optical signal reflected by the body part and displaying the physiological health information on the display unit by the processing unit.

In some embodiment, capturing the body part information of the user includes capturing the body part information when a distance between the body part and the sensing unit is less than a preset distance.

In some embodiment, receiving the optical signal reflected by the body part of the user by the sensing unit to capture the body part information of the user includes:

the sensing unit receiving a detection trigger signal and staying in a light detection status and receiving optical signal reflected by the body part to capture the body part information; wherein the light source trigger signal and the detection trigger signal are switched alternately at a preset frequency.

In some embodiment, capturing the body part information of user includes:

calculating a feature value based on the captured body part information of the user and comparing the calculated feature value with a preset feature value of the body part information; determining that the captured body part information matches successfully when an error is less than a preset value, otherwise determining that the captured body part information is failed to match.

In some embodiment, the method further includes:

generating a prompt message when it is determined that the captured body part information is failed to match.

In some embodiment, the prompt message further includes one or more of sound prompt information, image prompt information, light prompt information, and video prompt information.

In some embodiment, the sensing unit further includes TFT image sensing array film, and the TFT image sensing array film includes an array formed by photodiodes or phototransistors.

In some embodiment, light detected by the array formed by photodiodes or phototransistors includes visible light or infrared light.

In some embodiment, the TFT image sensing array film is an array formed by the photodiodes, the array formed by the photodiodes includes a photodiode sensing area, the photodiode sensing area includes a photodiode layer, the photodiodes layer includes a p-type semiconductor layer, a i-type semiconductor layer and a n-type semiconductor layer;

the p-type semiconductor layer, the i-type semiconductor layer and the n-type semiconductor layers are stacked in sequence;

the i-type semiconductor layer has a microcrystalline silicon structure or an amorphous germanium silicide structure.

In some embodiment, the microcrystalline silicon structure is a semiconductor layer formed by silane and hydrogen via chemical vapor deposition, a crystallinity of the microcrystalline silicon structure is higher than 40%, and the band gap of the microcrystalline silicon structure is less than 1.7 eV.

In some embodiment, the amorphous germanium silicide structure is an amorphous semiconductor layer formed by silane, hydrogen, and germane via chemical vapor deposition; the band gap of the amorphous semiconductor layer is less than 1.7 eV.

In some embodiment, further comprising a first optical element disposed on a top surface of the p-type semiconductor layer, wherein the first optical element is configured to reduce reflectivity of light on the top surface of the p-type semiconductor layer or reduce a refraction angle of light in the p-type semiconductor layer to increase amount of light incident.

In some embodiment, further comprising a second optical element disposed on the bottom surface of the n-type semiconductor layer, wherein the second optical element is configured to increase reflectivity of light on the bottom surface of the n-type semiconductor layer.

In some embodiment, the TFT image sensing array film is an array formed by the phototransistors, the array formed by the phototransistors includes a phototransistor sensing area;

a photosensitive film transistor is disposed on the phototransistor sensing area;

the photosensitive film transistor has an inverted coplanar structure, the inverted coplanar structure includes the gate, the insulating layer, the source are disposed vertically from bottom to top, the drain and the source are laterally coplanar; the insulating layer surrounds the source so that there is no contact between the gate, the source, and the drain;

the source and the drain are isolated by a gap;

a photosensitive leakage current channel is formed between the source and the drain laterally, the light absorbing semiconductor layer is disposed in the photosensitive leakage current channel.

In some embodiment, the number of the source and the drain are multiple, the sources are connected to each other in parallel; the drains are connected to each other in parallel;

the source and the drain are isolated by the gap, the photosensitive leakage current channel formed between the source and the drain laterally includes:

a first gap formed between the adjacent sources, one of the drains disposed in the first gap, a second gap formed between the adjacent drains, one of the sources disposed in the second gap;

the source and the drain are staggered and isolated by the gap.

In some embodiment, the display unit is a screen using the active array thin film transistor for driving scan and transmitting data; the screen includes a AMOLED display, a LCD display, a micro-LED display, a quantum dot display, or an electronic ink display.

In some embodiment, a backlight unit is disposed below the sensing unit when the display unit is LCD display or electronic ink display, the sensing unit is disposed between the LCD display and the backlight unit.

In some embodiment, the body part identification area includes a plurality of body part identification sub-area, a sensing unit is disposed below each body part identification sub-area.

In some embodiment, the device includes a sensing unit control circuit, the method further includes:

driving a sensing unit below a body part identification sub-area by the sensing unit control circuit when a start command of the body part identification sub-area is received; and shutting down a sensing unit below a body part identification sub-area by the sensing unit control circuit when a close command of the body part identification sub-area is received.

In some embodiment, the physiological health information includes one or more of blood pressure index, blood volume, body fat content, blood oxygen saturation, pulse rate, cardiopulmonary index, electrocardiogram.

The inventor further provides an operation device for physiological health detection. The device includes a display unit, a sensing unit and a processing unit; wherein a body part identification area is disposed on the display, the sensing unit is disposed below the body part identification area;

the sensing unit is configured to generate an optical signal, receive the optical signal reflected by the body part of the a user, capture a body part information of the user and record an optical signal information reflected by the body part when receiving a light source trigger signal;

the processing unit is configured to obtain a physiological health information corresponding to the body part based on the optical signal reflected by the body part and display the physiological health information on the display unit.

In some embodiment, capturing the body part information of user includes: capturing the body part information when a distance between the body part and the sensing unit is less than a preset distance.

In some embodiment, the sensing unit configured to receive the optical signal reflected by the body part of the user by the sensing unit to capture the body part information of user includes:

the sensing unit configured to receive a detection trigger signal and staying in a light detection status and receive optical signal reflected by the body part to capture the body part information;

the light source trigger signal and the detection trigger signal are alternately switched at a preset frequency.

In some embodiment, capturing the body part information of user includes:

the processing unit configured to calculate a feature value based on the captured body part information of the user and compare the calculated feature value with a preset feature value of the body part information; the processing unit configured to determine that the captured body part information matches successfully when an error is less than a preset value, otherwise determine that the captured body part information is failed to match.

In some embodiment, the device includes a prompt unit, the prompt unit generates a prompt message when the processing unit determines that the captured body part information is failed to match.

In some embodiment, the prompt message further includes one or more of sound prompt information, image prompt information, light prompt information, and video prompt information.

In some embodiment, the sensing unit further includes TFT image sensing array film, and the TFT image sensing array film includes an array formed by photodiodes or phototransistors.

In some embodiment, light detected by array formed by photodiodes or phototransistors includes visible light or infrared light.

In some embodiment, the TFT image sensing array film is an array formed by the photodiodes, the array formed by the photodiode includes a photodiode sensing area, the photodiode sensing area includes a photodiode layer, the photodiodes includes a p-type semiconductor layer, a i-type semiconductor layer and a n-type semiconductor layer;

the p-type semiconductor layer, the i-type semiconductor layer and the n-type semiconductor layers are stacked in sequence; and the i-type semiconductor layer has a microcrystalline silicon structure or an amorphous germanium silicide structure.

In some embodiment, the microcrystalline silicon structure is a semiconductor layer formed by silane and hydrogen via chemical vapor deposition, a crystallinity of the microcrystalline silicon structure is higher than 40%, and the band gap of the microcrystalline silicon structure is less than 1.7 eV.

In some embodiment, the amorphous germanium silicide structure is an amorphous semiconductor layer formed silane, hydrogen, and germane via chemical vapor deposition; the band gap of the amorphous semiconductor layer is less than 1.7 eV.

In some embodiment, further comprising a first optical element disposed on a top surface of the p-type semiconductor layer, wherein the first optical element is configured to reduce reflectivity of light on the top surface of the p-type semiconductor layer or reduce a refraction angle of light in the p-type semiconductor layer to increase amount of light incident.

In some embodiment, further comprising a second optical element is disposed on a bottom surface of the n-type semiconductor layer, the second optical element is configured to increase reflectivity of light on the bottom surface of the n-type semiconductor layer.

In some embodiment, the TFT image sensing array film is an array formed by phototransistor, the array formed by the phototransistors includes a phototransistor sensing area;

a photosensitive film transistor is disposed on the phototransistor sensing area, the photosensitive film transistor comprising a gate, a source, a drain, an insulating layer, and a light absorbing semiconductor layer;

the photosensitive film transistor has an inverted coplanar structure, the inverted coplanar structure comprising the gate, the insulating layer, the source are disposed vertically from bottom to top, the drain and the source are laterally coplanar; the insulating layer surrounds the source so that there is no contact between the gate, the source, and the drain;

the source and the drain are isolated by a gap;

a photosensitive leakage current channel is formed between the source and the drain laterally, the light absorbing semiconductor layer is disposed in the photosensitive leakage current channel.

In some embodiment, the number of the source and the drain are multiple, the number of the source and the drain are multiple, the sources are connected to each other in parallel; the drains are connected to each other in parallel;

the source and the drain are isolated by the gap, the photosensitive leakage current channel formed between the source and the drain laterally includes:

a first gap formed between the adjacent source;

one of the drains disposed in the first gap;

a second gap formed between the adjacent drain;

one of the sources disposed in the second gap, the source and the drain are staggered and isolated by the gap.

In some embodiment, the display unit is a screen using the active array thin film transistor as for driving scan and transmitting data;

the screen includes an AMOLED display, a LCD display, a micro-LED display, a quantum dot display, or an electronic ink display.

In some embodiment, a backlight unit is disposed below the sensing unit when the display unit is a LCD display or an electronic ink display; the sensing unit is disposed between the LCD display and the backlight unit.

In some embodiment, the body part identification area includes a plurality of body part identification sub-area, a sensing unit is disposed below each body part identification sub-area.

In some embodiment, the device further includes a sensing unit control circuit configured to receive a start command of the body part identification sub-area and drive a sensing unit below a body part identification sub-area;

the sensing unit control circuit configured to receive a close command of a body part identification sub-area and shut down a sensing unit below the body part identification sub-area.

In some embodiment, the physiological health information includes one or more of blood pressure index, blood volume, body fat content, blood oxygen saturation, pulse rate, cardiopulmonary index, electrocardiogram.

Therefore, the present disclosure has following advantages. By arranging a body part identification area on a display unit and arranging a sensing unit below the body part identification area, when a body part of a user is close to the body part identification area, a processing unit may obtain, according to the optical signal information reflected by the body part, physiological health information corresponding to the body part, and the physiological health information may be displayed on the display unit. Compared with the existing method of a mobile device additionally arranging a sensor outside a display screen region, the present disclosure facilitates user operations and improves the user experience, and the whole thickness of the mobile device may also be effectively reduced, thereby enabling the mobile device to be lighter and thinner and satisfy the requirements of the market.

DESCRIPTION OF THE PREFERRED EMBODIMENTS

In order to explain the technical content, structural features, achieved objectives, and effects of the technical solution in detail, the following describes it in detail with reference to specific embodiments and accompanying drawings.

Figure 1:
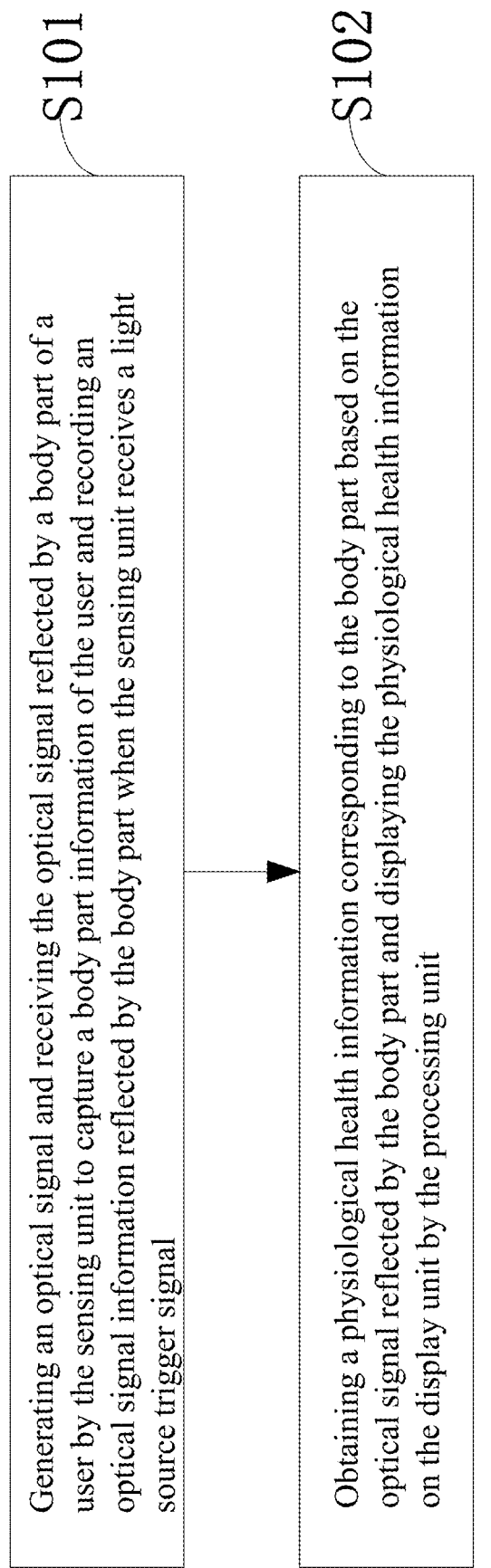
FIG. 1 is a flowchart of an operation method for physiological health according to an embodiment of the present disclosure.

Please refer to FIG. 1, FIG. 1 is a flowchart of an operation method for physiological health detection according to an embodiment of the present disclosure. The operation method for physiological health detection is applied to an operation device for physiological health including a display unit, a sensing unit and a processing unit. There is a body part identification area disposed on the display unit. The sensing unit is disposed below the body part identification area. The operation device for physiological health detection is an electronic device with a touch display screen, such as a smart mobile device such as a mobile phone, a tablet computer, a personal digital assistant, or an electronic device such as a personal computer or a computer for industrial equipment. The operation method includes the following steps:

First, a step S101 of generating an optical signal and receiving the optical signal reflected by a body part of a user by the sensing unit to capture a body part information of the user and recording an optical signal reflected by the body part when the sensing unit receives a light source trigger signal is executed.

The user body part, as the name implies, is a part of the user's body including the head, chest, hands, feet, etc., and can be specifically selected according to actual needs. For example, if the user wants to obtain the current own pulse rate, the user just places the pulse part close to the body part identification area.

Next, a step S102 of obtaining a physiological health information corresponding to the body part based on the optical signal information reflected by the body part and displaying the physiological health information on the display unit by the processing unit is executed.

The physiological health information includes any one or more of blood pressure index, blood volume, body fat content, blood oxygen saturation, pulse rate, cardiopulmonary index, and electrocardiogram. In this embodiment, the display unit is a screen using the active array film transistor for driving scan and transmitting data, and the screen includes an AMOLED display, a LCD liquid crystal display, a micro light emitting diode display, a quantum dot display, or an electronic ink display.

Some light will be absorbed, and some light will be reflected, scattered, etc. when the light passes through the human skin and into other tissues below the surface of the body. The change of the light path depends on the structure of the tissue below the skin. In general, human blood can absorb more light than surrounding tissues, so the less optical signal are reflected back when the optical signal encounter more blood the blood. Therefore, corresponding blood volume information of the user can be obtained via detecting the optical signal information reflected by the body part.

For the pulse rate, the blood volume of the human body generally increases or decreases with each beat of the pulse. Therefore, the processing unit can also analyze the reflected optical signal information to obtain the change information of the user's blood volume, and then the pulse rate data is obtained and displayed on the display unit. As for blood pressure index, body fat content, blood oxygen saturation, cardiopulmonary index, electrocardiogram, etc., the same can be obtained so they would not be repeated here. In short, by generating the optical signal from the sensing unit and detecting the reflected optical signal information, some current tissue structure information of the human body can be obtained, and then further analyzed and transformed by the processing unit to obtain corresponding physiological health information.

In some embodiments, the capturing the body part information of the user includes: capturing the body part information when a distance between the body part and the sensing unit is less than a preset distance. The sensing unit can determine the distance between the current user's body part and the sensing unit via detecting the time difference between the optical signal emitted and the optical signal reflected back. In other embodiments, the sensing unit may further determine whether the distance between the body part and the sensing unit is less than a preset distance via sensing a change in light intensity of the surrounding environment. the sensing unit captures the body part information only when the distance between the body part and the sensing unit is less than the preset distance. It can effectively avoid the user's wrong operation, more user-friendly, and improve the user's experience.

In some embodiments, capturing the body part information of the user includes: calculate a feature value based on the captured body part information of the user, and compare the calculated feature value with a preset feature value of the body part information. Determine that the captured body part information is matched successfully when the error is less than the preset feature value, otherwise, determine that the captured body part information is failed to match.

In some embodiment, the method further includes the step as: generate a prompt message when it is determined that the captured body part information is failed to match. The prompt information includes one or more of sound prompt information, image prompt information, light prompt information, and video prompt information. The sound prompt information includes voice prompt information prompting the user to bring the body part closer to the recognition area again. The image prompt information includes pop-up prompt information prompting the user to bring the body part closer to the recognition area again. The video prompt information includes animation prompt information prompting the user to bring the body part closer to the recognition area again. The light prompts include changing the screen brightness or making the display emit different colors of light, etc. In short, the prompt information mainly is used as a warning to inform the user that the sensor unit has not captured the body part information, so that the user can detect and process it early.

In some embodiments, the sensing unit includes a TFT image sensing array film, and the TFT image sensing array film includes an array formed by a photodiodes or a phototransistors. The light detection wavelength range of the array formed by the photodiodes or phototransistors includes a visible light or infrared light. The TFT image sensing array film is composed of M×N TFT image sensing films, and each TFT image sensing film corresponds to one pixel. Therefore, the TFT image sensing array film can be used to detect M×N pixels to form a corresponding image.

For each TFT image sensing film, there are several implementation methods:

First Embodiment

The TFT image sensing array film is an array formed by the photodiodes. The array formed by the photodiodes includes a photodiode sensing area. Existing liquid crystal display (LCD) panels or organic light emitting diode (OLED) display panels are driven by a TFT structure to scan a single pixel to achieve the display function of the pixel array on the panel. The main structure that forms the TFT switching function is a semiconductor field effect transistor (FET). The well-known semiconductor layer materials are mainly amorphous silicon, polysilicon, indium gallium zinc oxide (IGZO), or organic compounds mixed with carbon nanomaterials, etc. In recent years, TFT photo-detection diodes (i.e. photodiodes) have begun to be produced by TFT array preparation since the structure of the photo-sensing diode can also be prepared by using such semiconductor materials, and the production equipment is also compatible with the production equipment of the TFT array. For the specific structure of the existing photodiode, please refer to the description of the structure of the sensing unit in U.S. Pat. No. 6,943,070B2 and CN Pat. CN204808361U. The difference of the production process between the TFT image sensing array film and the display panel TFT structure is that light sensing area has replaced the original pixel opening area of the display panel in the production process. The TFT can be prepared by using thin glass or a high-temperature-resistant plastic material as a substrate as described in U.S. Pat. No. 6,430,070 B2.

Figure 2:
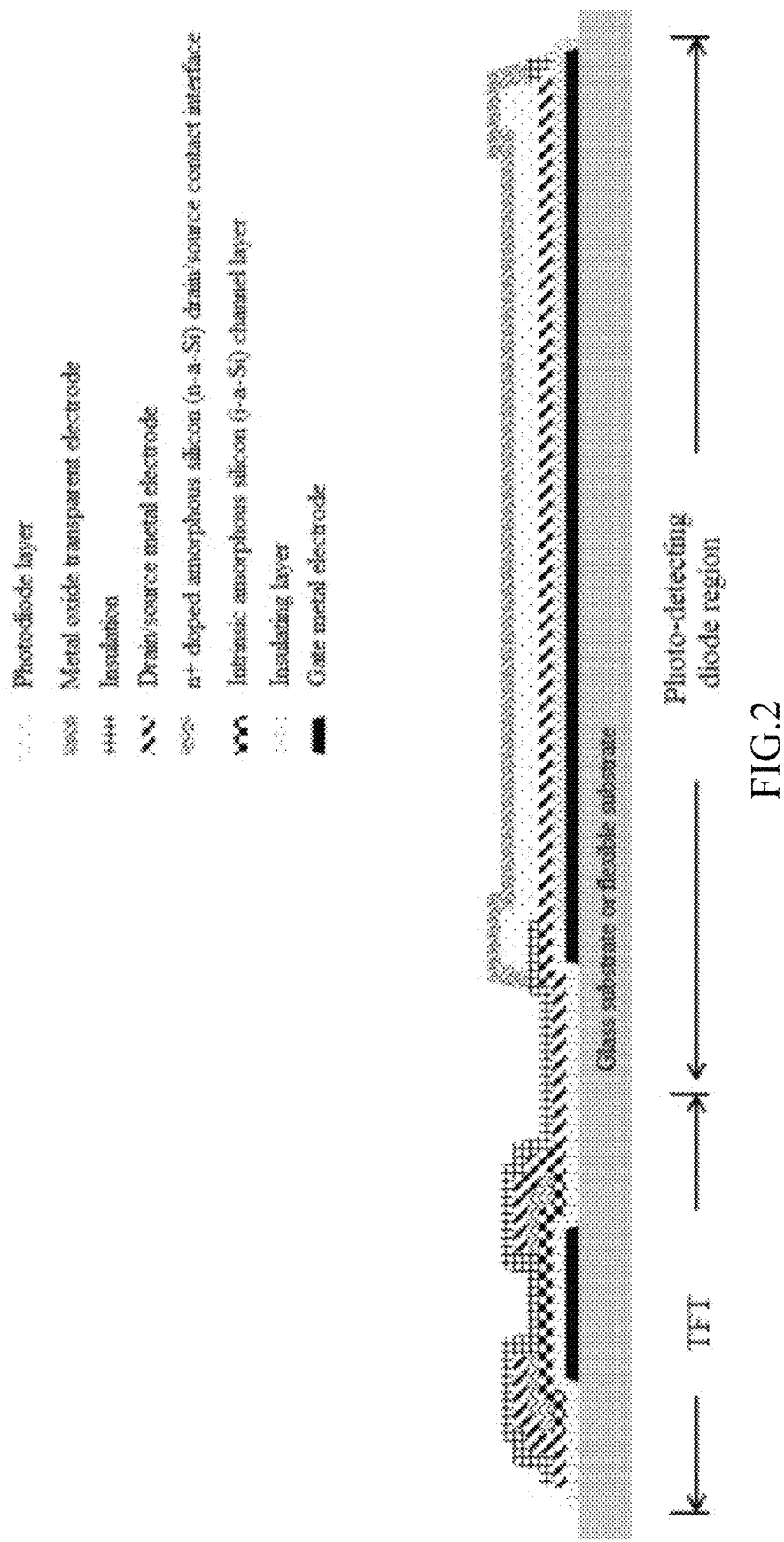
FIG. 2 is a schematic structural diagram of an embodiment of a TFT image sensing film of the present disclosure.

The existing TFT image sensing array film is susceptible to factors such as the surrounding ambient light or visible light reflection and refraction from the display pixels so it would cause optical interference and severely affecting the signal to noise ratio (SNR) of the TFT image sensing array film embedded under the display panel. In order to improve the SNR, as shown in FIG. 2, the sensing unit of the present disclosure is further improved, so that the TFT image sensing array film can detect and identify the infrared signal reflected by the user's body part. The specific structure is as follows:

The photodiode includes a p-type semiconductor layer, a i-type semiconductor layer and a n-type semiconductor layer. The p-type semiconductor layer, i-type semiconductor layer, and n-type semiconductor layer are stacked in sequence. The i-type semiconductor layer is a microcrystalline silicon structure or an amorphous germanium silicide structure. The microcrystalline silicon structure is a semiconductor layer formed by silane and hydrogen via chemical vapor deposition. The microcrystalline silicon structure is a semiconductor layer formed by silane and hydrogen via chemical vapor deposition, the crystallinity of the microcrystalline silicon structure is higher than 40%, and the band gap of the microcrystalline silicon structure is less than 1.7 eV. The amorphous germanium silicide structure is an amorphous semiconductor layer formed by silane, hydrogen, and germane via chemical vapor deposition; the band gap of the amorphous semiconductor layer is less than 1.7 eV.

The band gap is a width of forbidden band (unit is electron volts (eV)). The energy of electrons in solids cannot be continuously measured, because they are discontinuous energy bands. To conduct electricity, free electrons must be existed. The energy band which has free electron is called the conduction band (which can conduct electricity). To become a free electron, a bound electron must obtain sufficient energy to transition from the valence band to the conduction band. The minimum value of energy of transition is the band gap. The band gap is an important characteristic parameter of semiconductors. It's the value is mainly determined by the energy band structure of the semiconductor. It is related to the crystal structure and the bonding properties of atoms.

At room temperature (300K), the band gap of germanium is about 0.66 ev. Germanium is contained in silane. The band gap of i-type semiconductor layer will be reduced after doped with germanium. When the band gap is less than 1.7 eV, it means that the i-type semiconductor layer can receive optical signals in a wavelength range from visible light or infrared light (or near-infrared light). The operating wavelength range of photodiodes containing amorphous or microcrystalline germanium silicide structures can be extended to the range of light wavelengths from 600 nm to 2000 nm via adjusting the GeH4 concentration of chemical meteorological deposits.

Second Embodiment

On the basis of the first embodiment, in order to improve the quantum efficiency of photoelectric conversion, the amorphous silicon photodiode can also be formed by stacking p-type/i-type/n-type structures with a double junction or more. The p-type/i-type/n-type material of the first junction layer of the photodiode is still an amorphous silicon structure. The p-type/i-type/n-type material above the second junction layer may be a microcrystalline structure, a polycrystalline structure, or doped with compound materials that can extend the photosensitive wavelength range. In short, multiple groups of p-type/i-type/n-type structures can be stacked on top of each other to form a photodiode structure to achieve a photodiode structure. For each p-type/i-type/n-type structure, the photodiode structure described in the first embodiment is used.

Third Embodiment

On the basis of the first or second embodiment, for each p-type/i-type/n-type structure, the p-type semiconductor layer may be a multilayer structure with more than two layers. For example, the p-type semiconductor layer is a three-layer structure which includes a first p-type semiconductor layer (p1 layer), a second p-type semiconductor layer (p2 layer), and a third p-type semiconductor layer (p3 layer) in sequence. The p1 layer can adopt an amorphous structure and be heavily doped with boron (the boron concentration is more than twice that of the standard process). The p2 and p3 adopt a microcrystalline structure and are normally doped with boron (doped in accordance with the standard process concentration). The absorption of light can be reduced by the thinner p2 and p3 layers, so that light enters the i-layer as much as possible and is absorbed by the i layer to improve photoelectric conversion rate. On the other hand, the p2 layer and the p3 layer are normally doped with boron, which can effectively prevent the built-in potential from being deteriorated due to the heavy doping of p1 layer. When the p-type semiconductor layer includes a multi-layer structures having other numbers of layer, the structure is similar as other layer, and the details are not described again.

Similarly, the n-type semiconductor layer may have a multilayer structure with more than two layers. For example, the n-type semiconductor layer is a three-layer structure which includes a first n-type semiconductor layer (n1 layer), a second n-type semiconductor layer (n2 layer), and a third n-type semiconductor layer (n3 layer) in sequence. The n3 layer can adopt an amorphous structure and be heavily doped with phosphorus (the phosphorus content is more than twice that of the standard process). The n1 and the n2 adopt microcrystalline structure and are normally doped with phosphorus (according to standard production process). The absorption of light can be reduced by the thinner p2 and p3 layers, so that light enters the i-layer as much as possible and is absorbed by the i-layer to improve photoelectric conversion rate. On the other hand, the normal phosphorus doping of the n1 layer and the n2 layer can effectively prevent the built-in potential from being deteriorated due to the heavy doping of the n3 layer. When the n-type semiconductor layer includes a multi-layer structure having other numbers of layer, the structure is similar as other layers, and the details are not described again.

Fourth Embodiment

Figure 7:
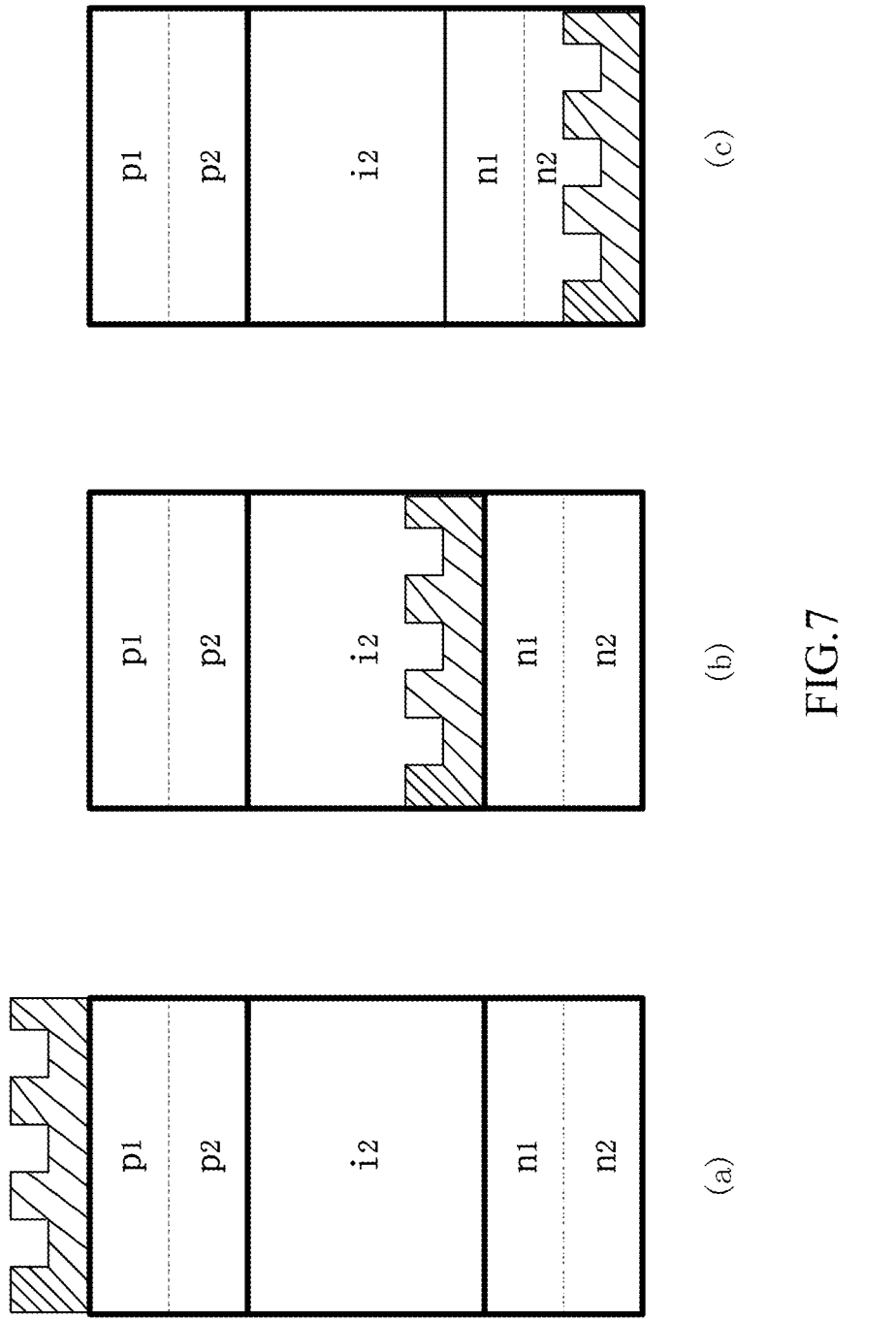
FIG. 7 is a schematic diagram of an embodiment of distribution of optics of the present disposure.

This embodiment is a further improvement of the first, second or third embodiment. As shown in (a) of FIG. 7, specifically, a first optical element is disposed on a top surface of the p-type semiconductor layer. The first optical element is configured to reduce reflectance of light on the top surface of the p-type semiconductor layer or reduce refraction angle of light in the p-type semiconductor to increase the amount of light incident. Reducing the angle of refraction of light in the p-type semiconductor layer allows the light to enter the p-type semiconductor layer as close to the vertical direction as possible, so that the light is absorbed as much as possible by the i-type semiconductor layer below the p-type semiconductor layer, thereby the photoelectric conversion rate of the photodiodes is further improved. the first optical element is disposed on the top surface of the uppermost p-type semiconductor layer when the p-type semiconductor layer is a multilayer structure.

The first optical element includes a photonic crystal structure with a periodically changing refractive index, micro lens array structure or diffuse scattering structure with aperiodic change of refractive index. The refractive index of the first optical element is lower than the refractive index of the p-type semiconductor layer, so that the incident angle is lower than the refractive angle after the light is refracted by the first optical element. That means the light enters the p-type semiconductor layer as close to the vertical direction as possible.

Fifth Embodiment

This embodiment is a further improvement of the fourth embodiment. As shown in (b) (c) in FIG. 7, a second optical element is further disposed on the bottom surface of the n-type semiconductor layer. The second optical element is configured to increase the multiple reflectance of light on the bottom surface of the n-type semiconductor layer. The multiple reflectance means that the light enters the i-type semiconductor layer after being reflected by the second optical element and is absorbed by the i-type semiconductor layer. The absorbed light enters the i-type semiconductor layer after being reflected again by the second optical element. This is repeated many times to improve the photoelectric conversion rate of the i-type semiconductor layer. The second optical element is disposed on the bottom surface of the lowermost n-type semiconductor layer when the n-type semiconductor layer is a multilayer structure.

The second optical element includes a photonic crystal structure with a periodically changing refractive index or a diffuse scattering structure with aperiodic change of refractive index. The refractive index of the second optical element is lower than the refractive index of the n-type semiconductor layer. In this way, the light can be reflected as much as possible on the bottom surface of the n-type semiconductor layer, so that the reflected light is absorbed again by the i-type semiconductor layer, thereby the signal in the wavelength range of light absorbed by i-type semiconductor is appropriately amplified to increase the photoelectric flux in this wavelength range.

Sixth Embodiment

Figure 3:
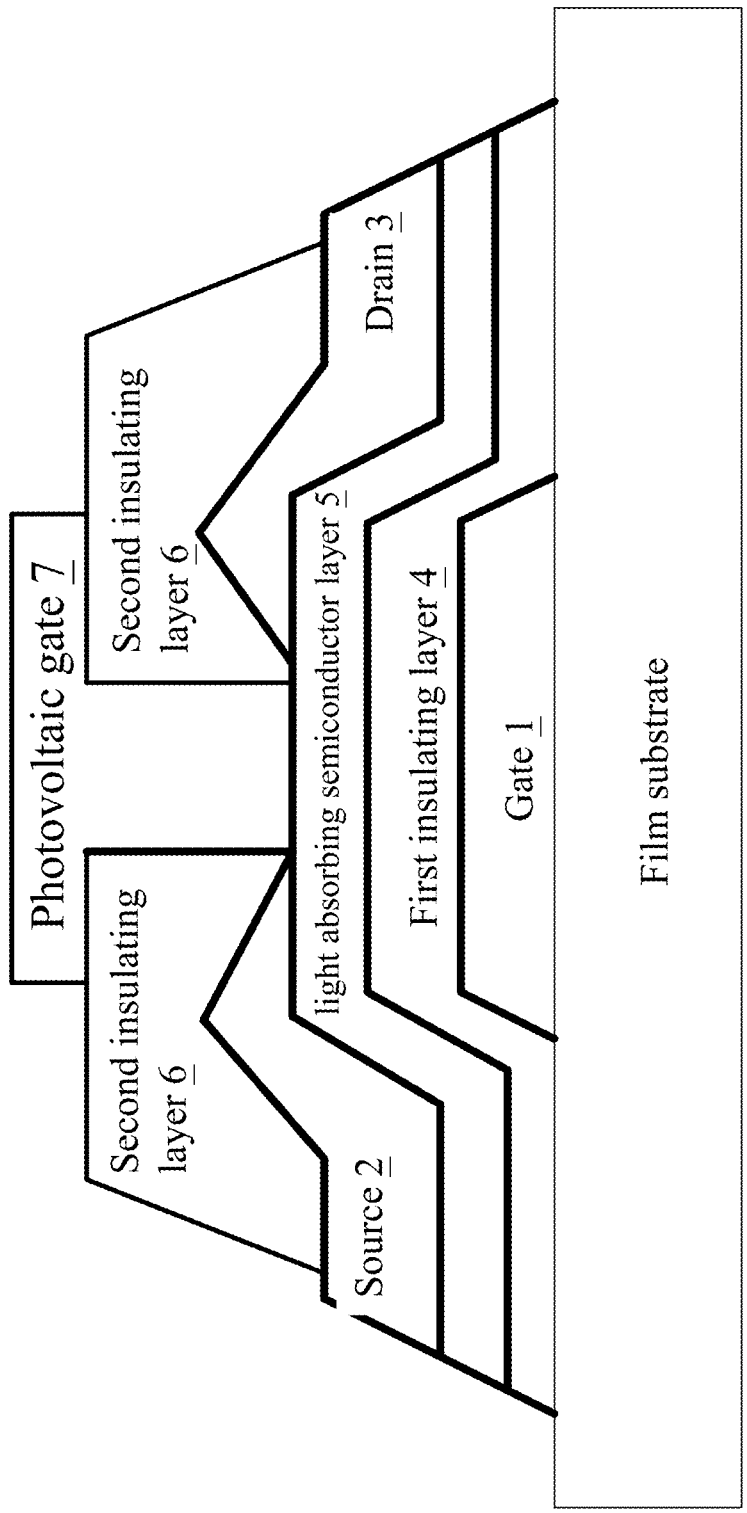
FIG. 3 is a schematic structural diagram of another embodiment of a TFT image sensing film of the present disclosure.

As shown in FIG. 3, the TFT image sensing array film is an array formed by the phototransistors. The array formed by the phototransistor includes a phototransistor sensing area. A photosensitive film transistor is disposed on the phototransistor sensing area of the phototransistors. The photosensitive film transistor includes a gate 1, a source 2, a drain 3, an insulating layer 4, and a light absorbing semiconductor layer 5. The photosensitive film transistor is an inverted coplanar structure. The inverted coplanar structure includes the gate 1, the insulating layer 4, and the source 2 vertically arranged in sequence. The drain electrode 3 and the source electrode 2 are laterally coplanar. The insulating layer 4 surrounds the gate 1 so that there is no contact between the gate 1 and the source 2, the gate 1 and the drain 3. The source 2 and the drain 3 are isolated by the gap. A photosensitive leakage current channel is formed between source 2 and drain 3 laterally. The light absorbing semiconductor layer 5 is disposed in the photosensitive leakage current channel.

Generally, no current will flow between the source and the drain when the TFT is controlled by the gate voltage to operate in the off state. However, the electron-hole pair is excited by the energy of the light in the semiconductor when the TFT is irradiated by a light source. The field effect of the TFT structure will cause the electron-hole pair separation, so that a photosensitive leakage current is generated on the TFT. This photosensitive leakage current characteristic allows the TFT array to be applied to light detection or light detection technology. Compared with a general device that uses TFT leakage current as a photosensitive film transistor, is a light absorbing semiconductor layer on the uppermost light absorbing layer by the inverted coplanar field effect transistor structure in the present disclosure. That greatly increases the excitation of photoelectrons and improves the photoelectric conversion efficiency.

Figure 8:
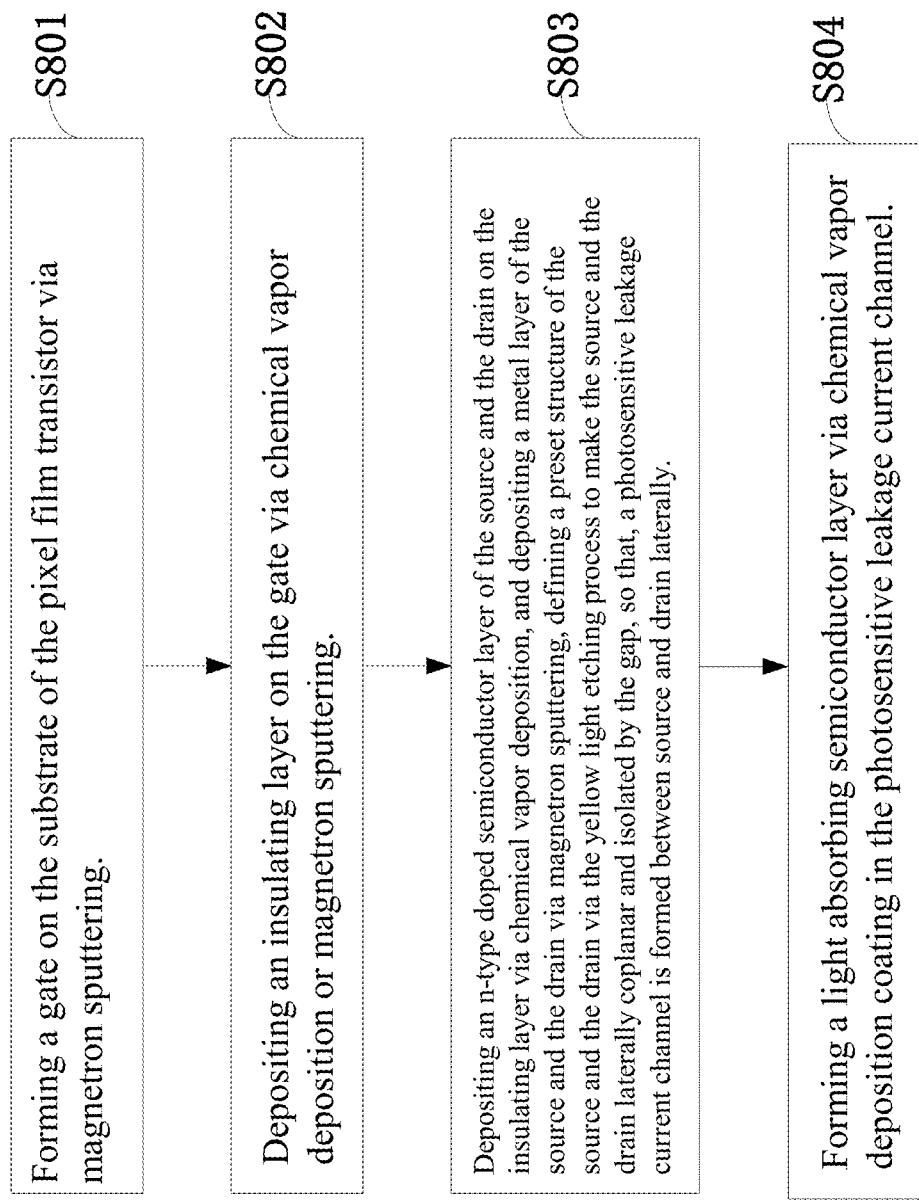
FIG. 8 is a flowchart of an embodiment of preparation method of light detection film of the present disposure.
Figure 9:
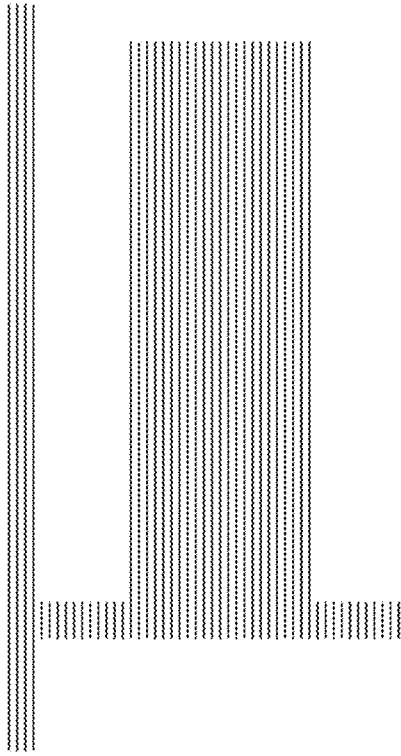
FIG. 9 is a flowchart of an embodiment of light detection film during preparation of the present disposure.
Figure 9:
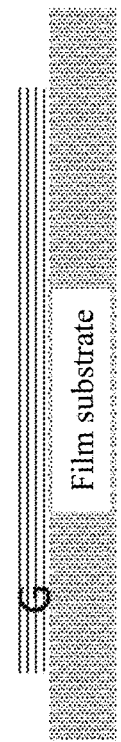
Figure 10:
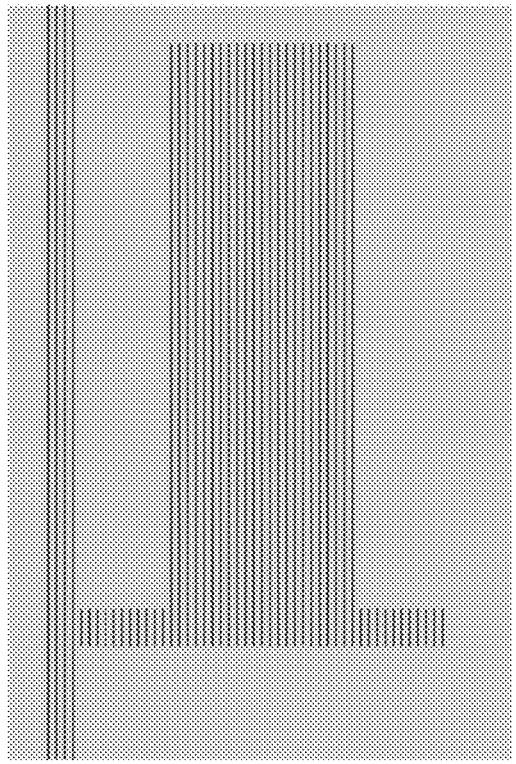
FIG. 10 is a flowchart of another embodiment of light detection film during preparation of the present disposure.
Figure 10:
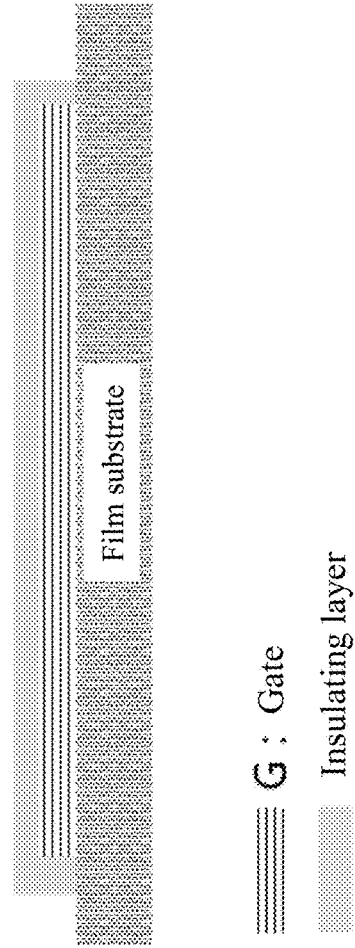
Figure 11:
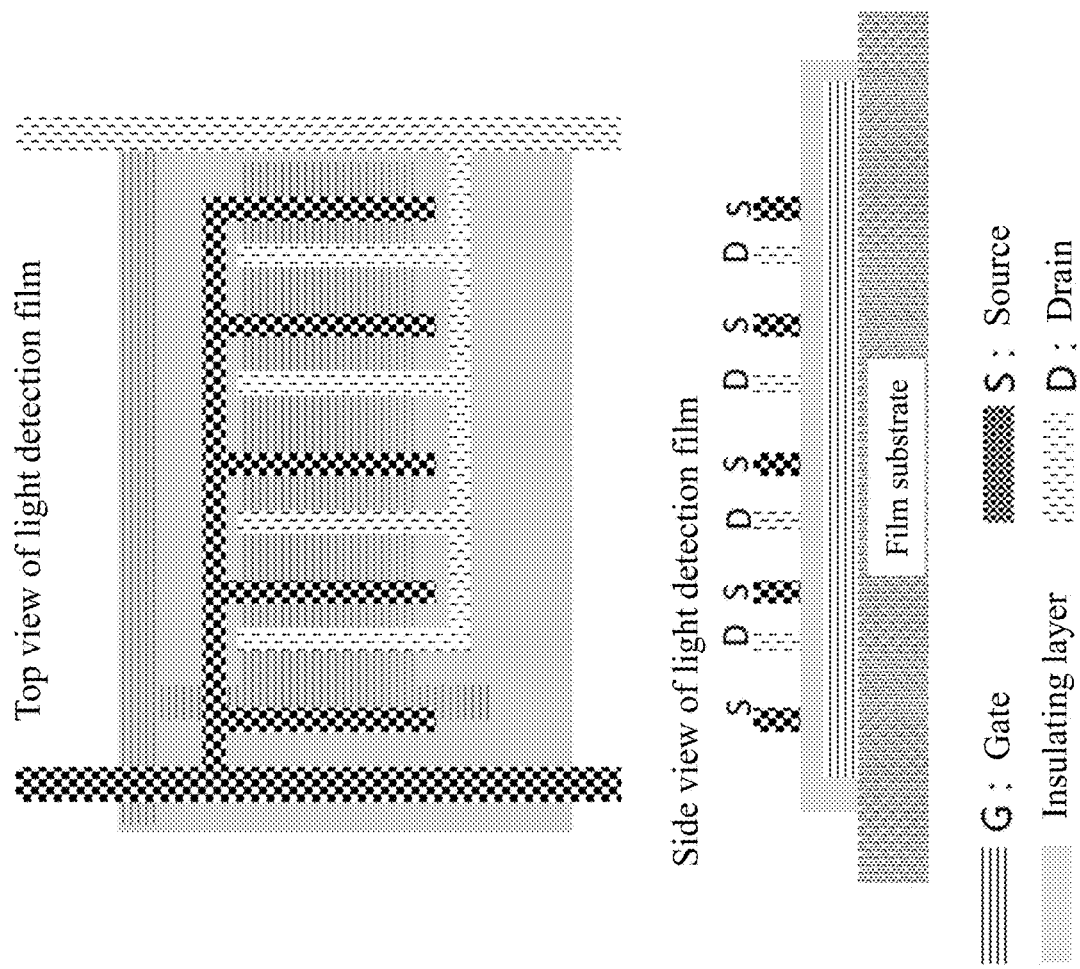
FIG. 11 is a flowchart of another embodiment of light detection film during preparation of the present disposure.
Figure 12:
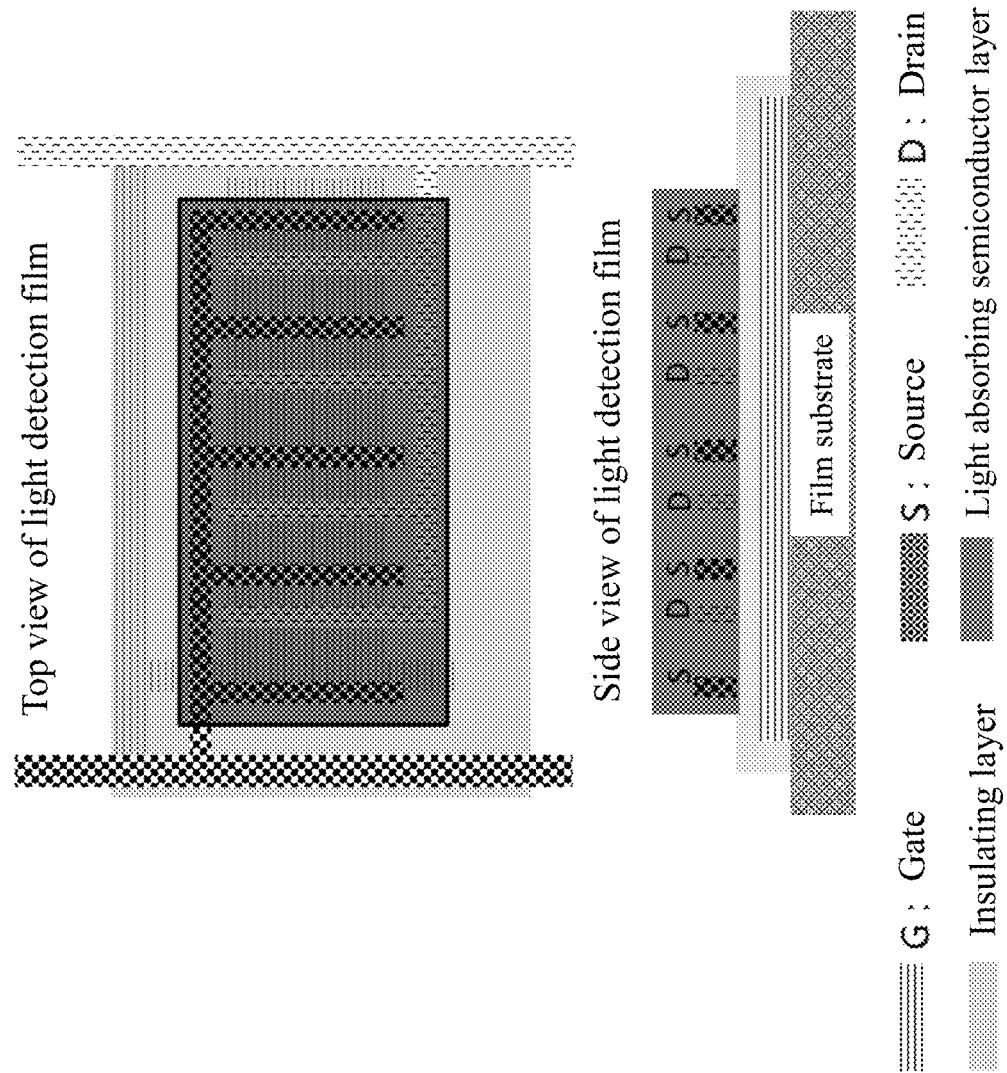
FIG. 12 is a flowchart of another embodiment of light detection film during preparation of the present disposure.

As shown in FIG. 8, it is a flowchart of an embodiment of a method for preparing light detection film of the present disclosure. The method is configured to prepare a photosensitive film transistor (i.e, a light detection film) of the sixth embodiment, and includes the following steps:

First, a step S801 of forming a gate on the substrate of the pixel film transistor via magnetron sputtering. The substrate of the pixel film transistor can be a rigid board or a flexible material (such as polyimide) is executed.

Next, a step S802 of depositing an insulating layer on the gate via chemical vapor deposition or magnetron sputtering is executed.

Next, a step S803 of depositing an n-type doped semiconductor layer of the source and the drain on the insulating layer via chemical vapor deposition, and depositing a metal layer of the source and the drain via magnetron sputtering, defining a preset structure of the source and the drain via the yellow light etching process to make the source and the drain laterally coplanar and isolated by the gap, so that, a photosensitive leakage current channel is formed between source and drain laterally is executed.

Next, a step S804 of forming a light absorbing semiconductor layer via chemical vapor deposition coating in the photosensitive leakage current channel is executed.

Seventh Embodiment

In terms of the familiar field effect transistor structure, the TFTs as scan drive and data transfer switches do not need to be designed specifically for the structure that collects photocurrent between the source and drain. However, in the application of field effect transistor in the detection of photosensitive leakage current, if the electron-hole pair excited by light is separated by field effect, the drift path driven by the electric field is too long, it is very likely that the photoelectrons will recombine with the holes or trapped by the dangling bond defect of the light absorbing semiconductor layer itself before they successfully reach the electrode. Thus, photocurrent output cannot be effectively used for photodetection.

In order to improve the photosensitive leakage current affected by the channel length between the source and the drain, so as to increase the area of the light-absorbing semiconductor without deteriorating the photoelectric conversion efficiency. In this embodiment, the source and the drain of the fourth embodiment are further improved, and a new structure of the source and the drain is proposed.

Figure 4:
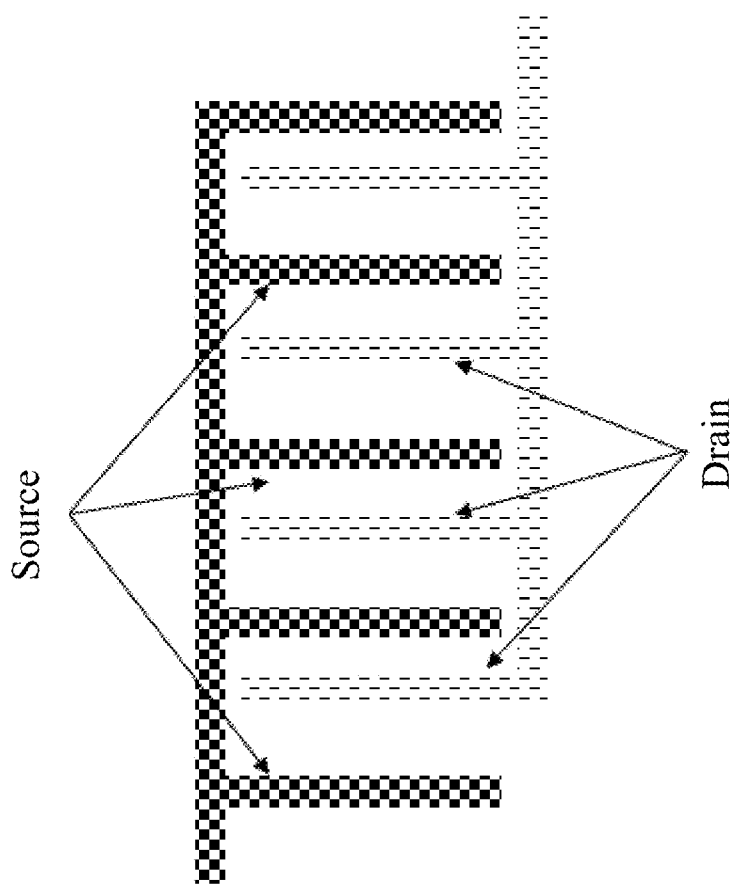
FIG. 4 is a schematic structural diagram of another embodiment of source and drain structure coordination of the present disclosure.

As shown in FIG. 4, the number of the source and drain are multiple. The sources are connected in parallel with each other, and the drain are connected in parallel with each other. The source and the drain are isolated by the gap. The photosensitive leakage current channel is formed between the source and drain laterally. The photosensitive leakage current channel includes a first gap formed between adjacent sources, a drain is placed in the first gap and a second gap formed between adjacent drains. The source and drain are staggered and isolated by the gap. The distance between each source and the adjacent drain is less than the electron drift distance. The electron drift distance is a distance that an electron can survive under a field effect. In this way, in each detection pixel, multiple sources belonging to the same pixel are connected in parallel to each other, and multiple drains belonging to the same pixel are also connected in parallel to each other. It can effectively reduce the probability of photo-excited electrons and holes recombining. The probability of the photoelectron being collected by the electrode under the field effect is improved, and the photosensitivity of the TFT leakage current photosensitive film transistor is improved maximumly.

As shown in FIGS. 9 to 12, in order to gradually prepare the process of the photosensitive film transistor (ie, the light detection film) of the seventh embodiment, the general steps are similar to the photosensitive film transistor of the sixth embodiment. The difference is that the "Define a preset structure of the source and drain via the yellow light etching process to obtain source and drain laterally coplanar and isolated by the gap" of the step S803 includes a source group and a drain group are defined by a yellow light etching process when the source and the drain are prepared. Each source group includes multiple sources connected in parallel with each other. A first gap is formed between adjacent sources, a drain is placed in the first gap. A second gap is formed between adjacent drains, and a source is disposed in the second gap. The source and the drain are staggered and isolated by the gap.

In some embodiment, the receiving the optical signal reflected by the user's body part and capturing the user's body part information includes: the sensing unit receives a detection trigger signal in a light detection state, and receives an optical signal reflected from a user's body part to capture user's body part information. The light source trigger signal and the detection trigger signal are alternately switched at a preset frequency. Taking the array formed by the sensing unit as a photodiode as an example, in the actual application process, the TFT can be used as a scanning to drive a bias voltage (including a forward bias voltage, a zero bias voltage or a negative bias voltage) between the p-type/i-type/n-type photodiode, so that function of TFT image sensing array film emitting infrared light can be achieved.

Specifically, a forward bias a zero bias or a negative bias may be applied between the p-type/i-type/n-type infrared photodiodes alternately to trigger the first trigger signal or the second trigger signal. Taking an array formed by infrared photodiodes with 10 pixel dots as an example, a forward bias is applied to the p-type/i-type/n-type infrared photodiodes during the first period, so that the 10-pixel pixel arrays are all emitting infrared light state. A zero or negative bias is applied to the p-type/i-type/n-type infrared photodiodes in the second period, so that the 10-pixel array is in the infrared light detection state, which is configured to capture the infrared light reflected by the user's eye information and generate corresponding infrared image output. In the third period, a forward bias is applied to the p-type/i-type/n-type infrared photodiodes, so that the 10-pixel pixel arrays are all in the state of emitting infrared light, alternating alternately, and so on. Further, the light source trigger signal (that is, the first trigger signal) and the detection trigger signal (that is, the second trigger signal) are alternately switched, and the switching frequency conforms to a preset frequency. The time interval between adjacent periods can be set according to actual needs. In some embodiment, the time interval can be set to the time required for the infrared photodiode array to receive at least one complete image signal when the TFT array drives and scans each frame, that is, the preset frequency is switched once after the above time interval has passed.

Figure 6:
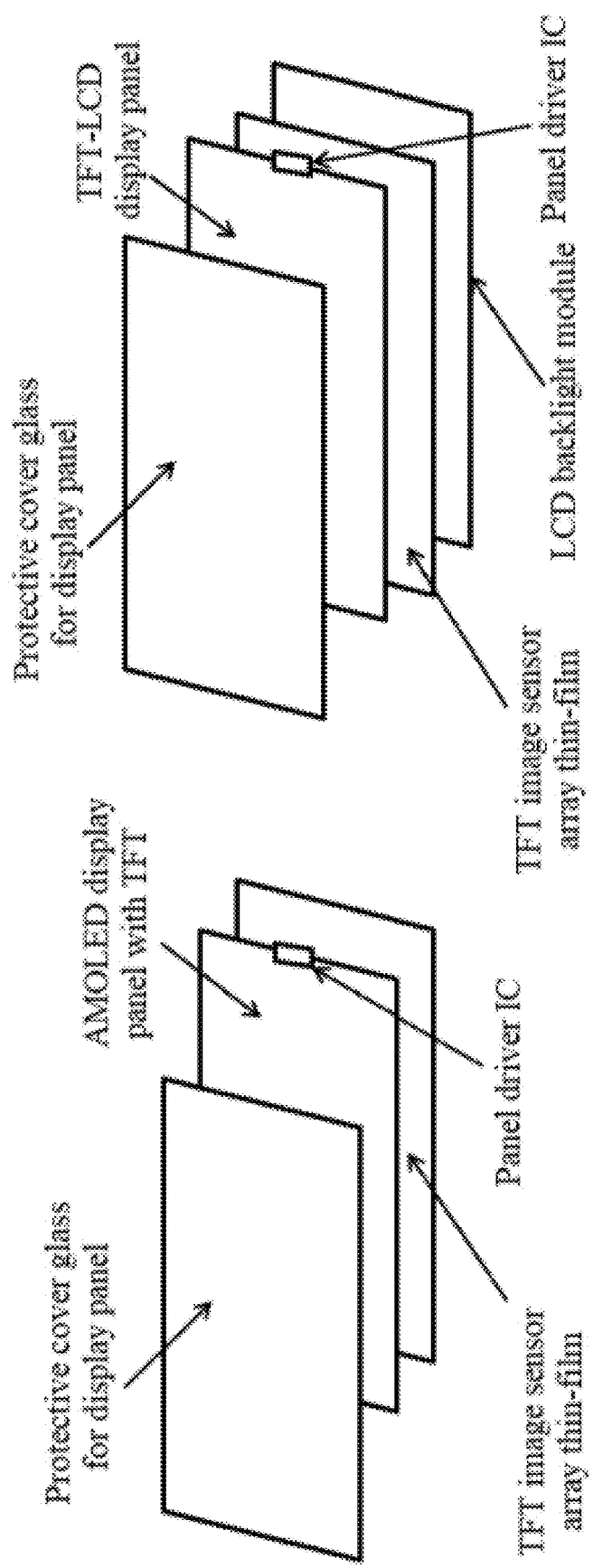
FIG. 6 is a schematic diagram of an embodiment of application scenario operating device for physiological health detection of the present disposure.

As shown in FIG. 6, a backlight unit is further disposed below the sensing unit (ie, the TFT image sensing array film in FIG. 6) when the display unit is an LCD or an electronic ink display. The sensing unit is disposed between the backlight unit and the LCD display. Since the LCD is not a self-luminous element, a backlight unit needs to be added below the sensing unit during installation. The backlight unit may be an LCD backlight module or other electronic components with a self-light-emitting function. In other embodiments, the OLED display screen is a self-luminous element when the display unit is an AMOLED display screen so there is no need to provide a backlight unit. The settings of the above two schemes can effectively meet the production needs of different manufacturers and increase the scope of application of the terminal.

In some embodiments, the body part identification area includes a plurality of body part identification sub-area, and a sensing unit is correspondingly disposed below each body part identification sub-area. The device further includes a sensing unit control circuit. The method further includes: the sensing unit control circuit drives the sensing unit below the body part identification sub-area after receiving a start command of the body part identification sub-area, and the sensing unit control circuit shuts down the sensing unit below the body part identification sub-area after receiving a close command of the body part identification sub-area.

Taking the number of body part identification sub-regions as two as an example, the two body part identification sub-area can be evenly distributed on the screen one by one or one left or right, or they can be distributed on the screen in other arrangements. The application process of a terminal with two body part identification sub-regions is specifically described below: a user-initiated activation signal is received during using, and the light detection devices (that is, the sensing unit) under the two body part identification sub sub-area are set to the on state. In some embodiment, the range formed by the two body part identification sub-areas coves the entire display screen. It can ensure that when the light detection devices under the two body part identification sub-areas are set to the on state. The light signal can be absorbed by the TFT image sensing array film (ie, the sensing unit) below to capture the user's fingerprint information.

In other embodiment, the range formed by the two body part identification sub-area can also cover ⅔, ¾, etc. of the entire display area. Of course, the user can also set the light detection device under one body part identification sub-area to turn on and the light detection device under another body part identification sub-area to turn off according to his own preference. When the terminal does not need to be operated, the light detection devices under the two body part identification subregions can also be set to the off state. In short, the light detection device under each body part identification sub-area is on or off and can be set according to the user's own preference.

Figure 5:
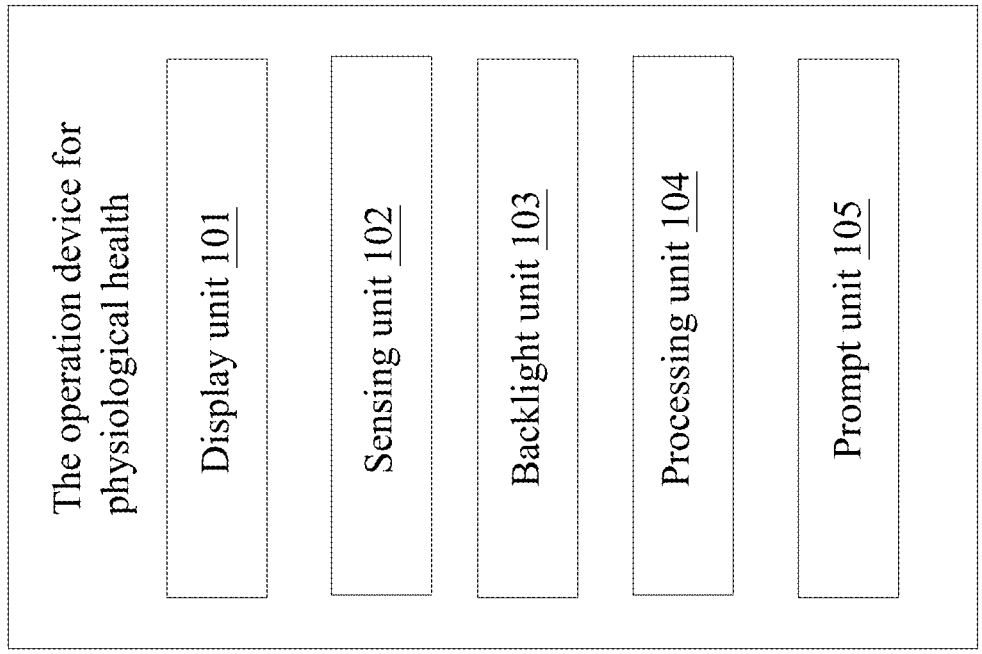
FIG. 5 is a schematic diagram of an embodiment of operating device for physiological health detection of the present disposure.

As shown in FIG. 5, it is a schematic diagram of an embodiment of operating device for physiological health detection of the present disposure. The device includes a display unit 101, a sensing unit 102, and a processing unit 10. A body part identification area is disposed on the display unit 101. The sensing unit 102 is disposed below the body part identification area.

The sensing unit 102 is configured to generate an optical signal and receive the optical signal reflected by the body part of the user to capture a body part information and record an optical signal information reflected by the body part when the sensing unit 102 is configured to receive the light source trigger signal.

The processing unit 104 is configured to obtain a physiological health information corresponding to the body part based on the optical signal information reflected by the body part and display the physiological health information on the display unit 101.

In some embodiment, the device includes a prompt unit 105. The prompt unit generates a prompt message when the processing unit determines that the captured body part information is failed to match. The prompt message further includes one or more of sound prompt information, image prompt information, light prompt information, and video prompt information.

In this embodiment, the display unit is a screen using the active array film transistor as a scanning driving and transmitting data. The screen includes an AMOLED display, a LCD display, a micro-LED display, quantum dot display, or an electronic ink display. As shown in FIG. 6, in some embodiments, a backlight unit disposed below the sensing unit, the sensing unit is disposed between the LCD display and the backlight unit when the display unit is the LCD display or the electronic ink display. Since the LCD is not a self-luminous element, a backlight unit needs to be added below the sensing unit during installation. The backlight unit may be an LCD backlight module or other electronic components with a self-light-emitting function. In other embodiments, there is no need to provide a backlight unit when the display unit is an AMOLED display screen, since the OLED display screen is a self-luminous element. The settings of the above two schemes can effectively meet the production needs of different manufacturers and increase the scope of application of the terminal.

The present disposure has the following advantages: by arranging a body part identification area on a display unit, and arranging a sensing unit below the body part identification area, when a body part of a user is close to the body part identification area, the sensing unit may capture optical signal information reflected by the body part, and a processing unit may obtain, according to the optical signal information reflected by the body part, physiological health information corresponding to the body part, and the physiological health information may be displayed on the display unit. Compared with the existing method of a mobile device additionally arranging a sensor outside a display screen region, the present invention facilitates user operations and improves the user experience, and the whole thickness of the mobile device may also be effectively reduced, thereby enabling the mobile device to be lighter and thinner and satisfy the requirements of the market.

I claim:

1. An operation device for physiological health detection comprises a display unit, a sensing unit and a processing unit; wherein a body part identification area is disposed on the display, the sensing unit is disposed below the body part identification area;

the sensing unit is configured to generate an optical signal, receive the optical signal reflected by the body part of a user, capture a body part information of the user and record an optical signal information reflected by the body part when receiving a light source trigger signal;

the processing unit is configured to obtain a physiological health information corresponding to the body part based on the optical signal reflected by the body part and display the physiological health information on the display unit;

wherein the sensing unit further comprises TFT image sensing array film, and the TFT image sensing array film comprises an array formed by photodiodes or phototransistors;

wherein light detected by array formed by photodiodes or phototransistors comprises visible light or infrared light;

wherein if the TFT image sensing array film is an array formed by the photodiodes, the array formed by the photodiode comprise a photodiode sensing area, the photodiode sensing area comprise a photodiode layer, the photodiodes comprise a p-type semiconductor layer, a i-type semiconductor layer and a n-type semiconductor layer;

the p-type semiconductor layer, the i-type semiconductor layer and the n-type semiconductor layers are stacked in sequence; and the i-type semiconductor layer has a microcrystalline silicon structure or an amorphous germanium silicide structure;

wherein if the TFT image sensing array film is an array formed by phototransistors, the array formed by the phototransistors comprise a phototransistor sensing area;

a photosensitive film transistor is disposed on the phototransistor sensing area, the photosensitive film transistor comprising a gate, a source, a drain, an insulating layer, and a light absorbing semiconductor layer;

the photosensitive film transistor has an inverted coplanar structure, the inverted coplanar structure comprising the gate, the insulating layer, the source are disposed vertically from bottom to top, the drain and the source are laterally coplanar; the insulating layer surrounds the source so that there is no contact between the gate, the source, and the drain;

the source and the drain are isolated by a gap;

a photosensitive leakage current channel is formed between the source and the drain laterally, the light absorbing semiconductor layer is disposed in the photosensitive leakage current channel.

2. The operation device for physiological health detection according to claim 1, wherein capturing the body part information of user comprises: capturing the body part information when a distance between the body part and the sensing unit is less than a preset distance.

3. The operation device for physiological health detection according to claim 1, wherein the sensing unit configured to receive the optical signal reflected by the body part of the user by the sensing unit to capture the body part information of user comprises:

the sensing unit configured to receive a detection trigger signal and staying in a light detection status and receive optical signal reflected by the body part to capture the body part information;

the light source trigger signal and the detection trigger signal are alternately switched at a preset frequency.

4. The operation device for physiological health according to claim 1, wherein capturing the body part information of user comprises:

the processing unit configured to calculate a feature value based on the captured body part information of the user and compare the calculated feature value with a preset feature value of the body part information; the processing unit configured to determine that the captured body part information matches successfully when an error is less than a preset value, otherwise determine that the captured body part information is failed to match.

5. The operation device for physiological health according to claim 4, wherein the device comprises a prompt unit, the prompt unit generates a prompt message when the processing unit determines that the captured body part information is failed to match.

6. The operation device for physiological health according to claim 5, wherein the prompt message further comprises one or more of sound prompt information, image prompt information, light prompt information, and video prompt information.

7. The operation device for physiological health according to claim 1, wherein if the TFT image sensing array film is an array formed by the photodiodes, the microcrystalline silicon structure is a semiconductor layer formed by silane and hydrogen via chemical vapor deposition, a crystallinity of the microcrystalline silicon structure is higher than 40%, and a band gap of the microcrystalline silicon structure is less than 1.7 eV.

8. The operation device for physiological health according to claim 1, wherein if the TFT image sensing array film is an array formed by the photodiodes, the amorphous germanium silicide structure is an amorphous semiconductor layer formed silane, hydrogen, and germane via chemical vapor deposition; the band gap of the amorphous semiconductor layer is less than 1.7 eV.

9. The operation device for physiological health according to claim 1, if the TFT image sensing array film is an array formed by the photodiodes, further comprising a first optical element disposed on a top surface of the p-type semiconductor layer, wherein the first optical element is configured to reduce reflectivity of light on the top surface of the p-type semiconductor layer or reduce a refraction angle of light in the p-type semiconductor layer to increase amount of light incident.

10. The operation device for physiological health according to claim 1, if the TFT image sensing array film is an array formed by the photodiodes, further comprising a second optical element is disposed on a bottom surface of the n-type semiconductor layer, the second optical element is configured to increase reflectivity of light on the bottom surface of the n-type semiconductor layer.

11. The operation device for physiological health according to claim 1, wherein if the TFT image sensing array film is an array formed by the phototransistors, the number of the source and the drain are multiple, the sources are connected to each other in parallel; the drains are connected to each other in parallel;

the source and the drain are isolated by the gap, the photosensitive leakage current channel formed between the source and the drain laterally comprising:

a first gap formed between the adjacent source;

one of the drains disposed in the first gap;

a second gap formed between the adjacent drain;

one of the sources disposed in the second gap, the source and the drain are staggered and isolated by the gap.

12. The operation device for physiological health according to claim 1, wherein the display unit is a screen using the active array film transistor as for driving scan and transmitting data;

the screen comprises an AMOLED display, a LCD display, a micro-LED display, a quantum dot display, or an electronic ink display.

13. The operation device for physiological health according to claim 12, wherein a backlight unit is disposed below the sensing unit when the display unit is a LCD display or an electronic ink display; the sensing unit is disposed between the LCD display and the backlight unit.

14. The operation device for physiological health according to claim 1, wherein the body part identification area comprises a plurality of body part identification sub-areas, a sensing unit is disposed below each body part identification sub-area.

15. The operation device for physiological health according to claim 14, wherein the device further comprises a sensing unit control circuit configured to receive a start command of the body part identification sub-area and drive a sensing unit below a body part identification sub-area;

the sensing unit control circuit configured to receive a close command of the body part identification sub-area and shut down a sensing unit below a body part identification sub-area.

16. The operation device for physiological health according to claim 1, wherein the physiological health information comprises one or more of blood pressure index, blood volume, body fat content, blood oxygen saturation, pulse rate, cardiopulmonary index, electrocardiogram.

\* \* \* \* \*